United States Patent

Isomura et al.

[11] Patent Number: 4,990,503
[45] Date of Patent: Feb. 5, 1991

[54] HETEROCYCLIC BISPHOSPHONIC ACID DERIVATIVES

[75] Inventors: Yasuo Isomura; Makoto Takeuchi; Tetsushi Abe, all of Ibaraki, Japan

[73] Assignee: Yamanouchi Pharmaceutical Co., Ltd., Tokyo, Japan

[21] Appl. No.: 390,090

[22] Filed: Aug. 7, 1989

[30] Foreign Application Priority Data

Aug. 12, 1988 [JP] Japan .................. 63-201535
Aug. 12, 1988 [JP] Japan .................. 63-201536

[51] Int. Cl.$^5$ .................. C07D 471/04; A61K 31/675
[52] U.S. Cl. .................................. 514/80; 546/23
[58] Field of Search .......................... 546/23; 514/80

[56] References Cited

U.S. PATENT DOCUMENTS

| | | | |
|---|---|---|---|
| 4,503,049 | 3/1985 | Biere et al. | 514/80 |
| 4,687,767 | 8/1987 | Bosies et al. | 514/80 |
| 4,777,163 | 10/1988 | Bosies et al. | 514/80 |
| 4,871,720 | 10/1989 | Jaeggi | 546/23 |

FOREIGN PATENT DOCUMENTS 0317505  5/1989  European Pat. Off. .......... 546/23

*Primary Examiner*—Mukund J. Shah
*Assistant Examiner*—E. C. Ward
*Attorney, Agent, or Firm*—Burgess, Ryan & Wayne

[57] ABSTRACT

A novel heterocyclic bisphosphonic acid derivatives represented by the following general formula (I):

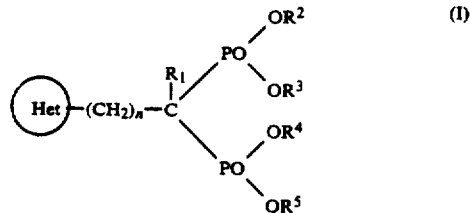

in which,
Het means one of following (A) and (B):

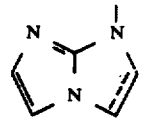

wherein a dotted line in (A) means that two adjacent atoms are bonded by a single bond or a double bond,

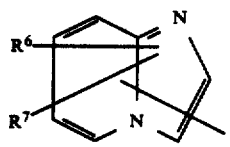

wherein $R^6$ and $R^7$ may be the same or different, each represents a hydrogen atom, a lower alkyl group, a halogen atom or a hydroxyl group,
$R^1$ represents a hydrogen atom or a hydroxyl group,
$R^2$, $R^3$, $R^4$ and $R^5$ may be the same or different, each represents a hydrogen atom or a lower alkyl group,
"n" is 0 or 1,
provided that "n" is 1 when the ring Het means (A), and "$R^1$" is a hydroxyl group when the ring Het means (B),
or pharmaceutically acceptable salts thereof and bone resorption inhibitors containing the compound as an active ingredient.

7 Claims, No Drawings

HETEROCYCLIC BISPHOSPHONIC ACID DERIVATIVES

BACKGROUND OF THE INVENTION

1. Field of the Invention

The present invention relates to novel heterocyclic bisphosphonic acid derivatives or pharmaceutically acceptable salts thereof and bone resorption inhibitors containing the compound as an active ingredient.

2. Description of the Related Art

A variety of compounds as bisphosphonic acid derivatives have been synthesized and known. However, the compounds having such a heterocyclic group as is defined by the present invention are novel compounds.

The present inventors found that the compounds represented by the general formula (I) or pharmaceutically acceptable salts thereof are novel compounds and have a bone resorption-inhibitory activity as well as an activity to inhibit hypercalcemia caused by bone resorption from the results of animal tests and thus the present invention was completed.

SUMMARY OF THE INVENTION

The present invention provides heterocyclic bisphosphonic acid derivatives represented by the following general formula (I):

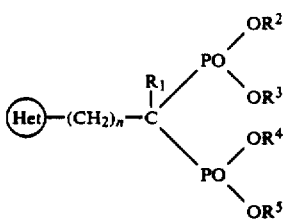

(I)

in which, $\text{Het}$ means one of following (A) and (B):

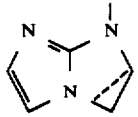

(A)

wherein a dotted line in (A) means that two adjacent atoms are bonded by a single bond or a double bond,

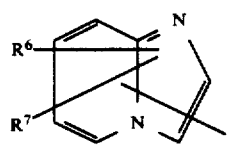

(B)

wherein $R^6$ and $R^7$ may be the same or different, each represents a hydrogen atom, a lower alkyl group, a halogen atom or a hydroxyl group, $R^1$ represents a hydrogen atom or a hydroxyl group, $R^2$, $R^3$, $R^4$ and $R^5$ may be the same or different, each represents a hydrogen atom or a lower alkyl group, "n" is 0 or 1, provided that "n" is 1 when the ring $\text{Het}$ means (A), and "$R^1$" is a hydroxyl group when the ring $\text{Het}$ means (B), or pharmaceutically acceptable salts thereof and bone resorption inhibitors containing the compound as an active ingredient.

In the definition of the groups in the general formula (I), the term "lower" means a linear or branched carbon chain having 1 to 5 carbon atoms if not mentioned otherwise. Therefore, the "lower alkyl group" may be methyl group, ethyl group, propyl group, isopropyl group, butyl group, isobutyl group, sec-butyl group, tert-butyl group, penty(amyl) group, iso-pentyl group, neopentyl group or the like.

The "heterocyclic group" represented by the formula (A):

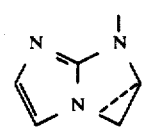

(A)

may be imidazo[1,2-a]imidazolyl group

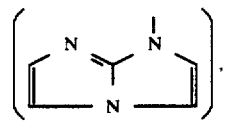

2,3-dihydroimidazo-[1,2-a]imidazolyl group

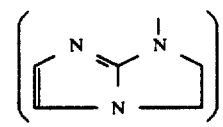

or the like.

The "heterocyclic group" represented by the formula (B):

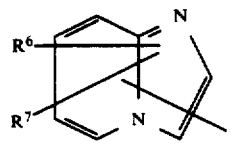

(B)

may be imidazo[1,2-a]pyridin-3-yl group

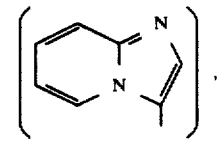

8-hydroxy-2-methylimidazo[1,2-a]pyridin-3-yl group

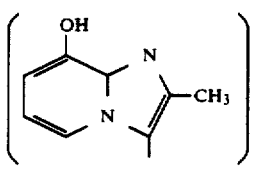

imidazo [1, 2-a] pyridin-2-yl group

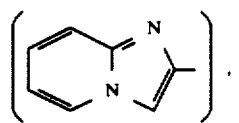

imidazo[1,2-a]pyridin-8-yl group

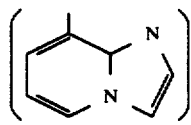

or the like.

The compounds (I) according to the present invention include tetraester of which $R^2$ to $R^5$ are lower alkyl groups or monoester, diester and triester of which one to three of $R^2$ to $R^5$ is a lower alkyl group or are lower alkyl groups.

The compounds according to the present invention form salts when they are free phosphonic acids. Therefore, the objective compounds of the present invention include pharmaceutically acceptable salts of the compounds (I). As preferable salts, it can be mentioned salts with inorganic bases such as salts with alkali metal, for example, sodium salts, potassium salts and salts with alkali earth metal, for example, calcium salts or magnesium salts; salts with organic bases such as ammonium salts, methylamine salts, ethylamine salts, dimethylamine salts, diethylamine salts, trimethylamine salts, triethylamine salts, cyclohexylamine salts, ethanolamine salts or diethanolamine salts; salts with basic amino acid such as lysine salts or ornithine salts or the like.

DESCRIPTION OF THE PREFERRED EMBODIMENTS

Preparing Methods of the Compounds

The compounds of the present invention can be prepared according to one of methods represented by the following reaction schema:

First Method

Compounds (Ia) of the formula (I) in which the ring (Het) means

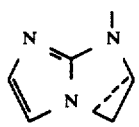

and $R^1$ is a hydrogen atom.

The compound represented by the general formula (Ia) can be obtained by reacting a compound represented by the general formula (II) with an ethylidene bisphosphonic acid derivative represented by the general formula (III) by the following reaction schema.

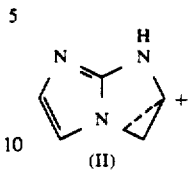

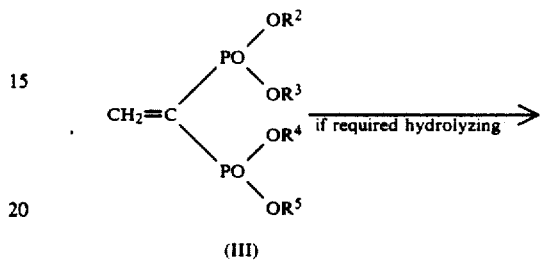

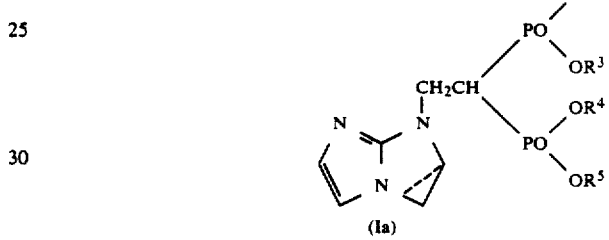

The reaction of the compounds (II) and (III) is effected in a solvent inactive to the reaction such as tetrahydrofuran, benzene, toluene, xylene or the like with such a proportion that an amount of the compound (III) with respect to the compound (II) is equal or excessive to the reaction formula. This reaction can be carried out without solvent.

The reaction is conducted at room temperature or under reflux. It is preferable to carry out the reaction with heating or under reflux.

The bisphosphonates obtained can be converted optionally to the corresponding bisphosphonic acids by hydrolysis. The hydrolysis is generally carried out by heating the bisphosphonates under reflux in concentrated hydrochloric acid. Alternatively, the hydrolysis can be effected by treating the bisphosphonates with a strong acid or a trimethylsilyl halide in a water-free solvent. This method is effected generally in a commercially available anhydrous hydrobromic acid dissolved in acetic acid directly or in a pertinently diluted solution thereof, or a solution of a trimethylsilyl iodide dissolved in a solvent such as carbon tetrachloride, dimethylformamide, chloroform, toluene or the like. The hydrolysis can be effected under cooling or heating. For example, when the ester is hydrolyzed with a trimethylsilyl halide with cooling at $-10°$ C. or lower, a partially hydrolyzed product is obtained.

When the bisphosphonic acids are converted to their salts, the acids are treated with a base such as sodium hydroxide, potassium hydroxide, ammonia, organic amine or the like by usual methods.

Second Method

Compounds (Ib) of the Formula (I) in Which $R^1$ is a Hydroxyl Group

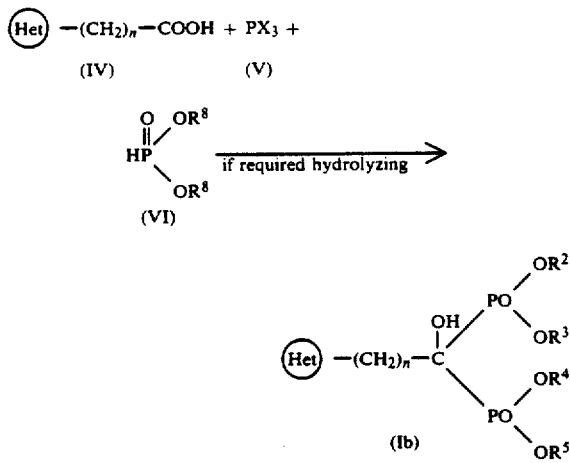

wherein the ring the ring (Het), $R^2$, $R^3$, $R^4$ and $R^5$ and "n" have the same definition as above, $R^8$ represents a hydrogen atom or a lower alkyl group and "X" represents a halogen atom.

The compound (Ib) having a hydroxyl group at the ethylene chain can be obtained by above-mentioned reaction schema.

In this reaction, a carboxylic acid derivative represented by the general formula (IV) is reacted with phosphorous trihalogenide (V) and with phosphorous acid (VI) or lower alkyl ester thereof. The halogen atoms may be chlorine atom, bromine atom, iodine atom or the like.

A mixed solution of carboxylic acid derivative (IV) and phosphorous acid or its ester (VI) is heated at first at 60 to 120° C., preferably at 80 to 110° C. for several minutes to several hours. Then, phosphorus trihalogenide (V) is added to the reacted mixed solution which is then heated at 60 to 120° C., preferably at 80 to 110° C. for several hours. The progress of the reaction can easily be traced by TLC (thin layer chromatography, with a developing system of chloroformmethanol).

The bisphosphonates thus obtained can be, if required, converted to their salts according to the process as mentioned above.

The isolation and purification of the desired product (I) can be carried out by usual chemical treatments such as extraction, crystallization, a variety of chromatographic operations or the like.

Inhibitory Effect on Hypercalcemia

The compounds (I) and their salts provided by the present invention have a bone resorption-inhibitory activity and also have an activity for inhibiting hypercalcemia caused by bone resorption. In addition, these are recognized to have excellent anti-inflammatory action and analgestic action.

Experimental test methods and results will be described hereunder so as to support the inhibitory effect on hypercalcemia of the compounds of the present invention and comparative compounds (C1) and (C2).

Rats of hypercalcemia induced by administration of parathyroid hormone were used and the decrement of the serum calcium amount by administration of the compound was measured.

Test Method

Human 1-34 parathyroid hormone (PTH, manufactured by Peptide Laboratory) which was dissolved in a 0.1% BSA (bovine serum albumin)-containing physiological saline was intravenously injected in an amount of 30 μg/kg (5 ml/kg as the solution) to 5-week-old male Wistar rats which had been fasting for 20 hours. To a normal control group, 0.1% BSA-containing physiological saline alone was injected in the same manner. 45 minutes after the PTH injection, the rats were etherized and then subjected to celiotomy in order to collect blood from the abdominal cava with a vacuum blood-collecting tube. The blood collected was immediately centrifuged by 3,000 rpm at 4° C. for 10 minutes to isolate the serum. The concentration of ionized calcium ($Ca^{++}$) in the serum was immediately measured in a $Ca^{++}$ meter (Sera 250, manufactured by Horiba Manufacturing Co.).

For subcutaneous administration, the compounds of the present invention were dissolved in physiological saline and pH was adjusted to 7.4 with sodium hydroxide and hydrochloric acid. For oral administration, a 5 ml/kg physiological saline solution of pH 7.4 was prepared. The solutions were administered 72 hours before the PTH injection. In the same manner, a physiological saline alone was administered to the normal control group and the control group.

The results for each group were expressed in terms of mean ±S.E. (standard error) and comparison was made among the groups by testing by one-way analysis of variance. The significance level was taken at 5%.

Results

The results obtained by the subcutaneous and by oral administration are shown in Table 1.

TABLE 1

| | Dose (mg/kg) | Method of Administration | N | Serum $Ca^{++}$ (m mol/liter) |
|---|---|---|---|---|
| Normal Control | — | sc | 5 | 1.26 ± 0.04** |
| Control | — | sc | 5 | 1.38 ± 0.02 |
| Compound of Example 3 | 0.03 | sc | 5 | 1.37 ± 0.02 |
| | 0.1 | sc | 5 | 1.35 ± 0.02 |
| | 0.3 | sc | 5 | 1.30 ± 0.01* |
| Normal Control | — | po | 5 | 1.37 ± 0.02 |
| Control | — | po | 4 | 1.41 ± 0.02 |
| Compound of Example 3 | 100 | po | 5 | 1.37 ± 0.02 |
| | 300 | po | 5 | 1.32 ± 0.01* |
| Normal Control | — | po | 5 | 1.35 ± 0.01 |
| Control | — | po | 5 | 1.43 ± 0.01 |
| Compound of Example 5 | 0.001 | sc | 5 | 1.38 ± 0.02 |
| | 0.003 | sc | 5 | 1.26 ± 0.02** |
| | 0.01 | sc | 5 | 1.08 ± 0.02** |
| | 3 | po | 5 | 1.35 ± 0.01 |
| | 10 | po | 5 | 1.26 ± 0.03** |

Mean value: ± S.E. *: $P < 0.05$ **: $P < 0.01$

From the results of tests, the compounds according to the present invention were demonstrated to have an excellent action for reducing the amount of serum calcium. Accordingly, it is confirmed that the compounds of the present invention have a bone resorption inhibitory action. As diseases considered to be caused by an excessive bone-resorption, there may be mentioned Paget's disease, hypercalcemia, metastatic osteocarcinoma, and osteoporosis. Sthenic bone resorption in inflammatory arthritides such as rheumatoid arthritis is also a big problem from a clinical point of view. The compounds provided by the present invention can be used as remedial medicines for these diseases to inhibit the bone resorption and to prevent the reduction of the bone amount or to prevent or reduce the rising of the serum calcium value caused by the sthenic bone resorption.

The compounds (I) of the present invention and their salts can be used as they are or are blended with any pharmaceutically acceptable carrier, vehicle, attenuant or the like to be formed into medical compositions, such as tablets, capsules, powder, granules, pills or the like for oral administration and injection solution, syrup, suppositories, ointment or the like for non-oral administration. The amount of the dose of the compounds (I) of the present invention is, although varying in accordance with the administration route, patient's symptom, etc., generally from 1 mg/day/adult to 1 g/day/adult for oral administration and from 0.1 to 10 mg/day/adult for non-oral administration.

Now the present invention will be described in more details with reference to Examples.

EXAMPLE 1

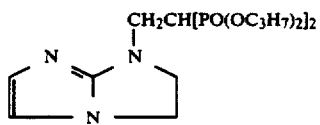

0.6 g of 5,6-dihydro-7H-imidazo[1,2-a] imidazole and 3.0 g of tetraisopropylethylidenebis(phosphonate) dissolved in 2 ml of tetrahydrofuran were heated under reflux for 6 hours. The reaction solution was concentrated under a reduced pressure. Then, the residue was purified on silica gel column chromatography (methanol/chloroform=1/39) to give 2.3 g of tetraisopropyl-2-(2,3-dihydro-1H-imidazo[1, 2-a]imidazol-1-yl)ethane-1,1-bis(phosphonate) as a yellow oil.

The physico-chemical characteristics of this product are as follows:

(i) Mass Spectrum (m/z): FAB Mass 466 (M+ +1)
(ii) Nuclear Magnetic Resonance Spectrum in CDCl$_3$, TMS internal standard):

| δ: | 2.96 | (1H, —CH$_2$CH—) |
|---|---|---|
| | 3.94 | |
| | (4H, | 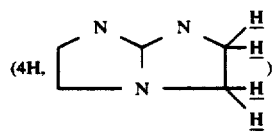 ) |
| | 6.53, 6.68 | (2H, aromatic H) |

In the same manner as Example 1, the following compounds were prepared.

EXAMPLE 2

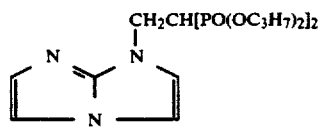

Tetraisopropyl-2-(imidazo[1,2-a]imidazol-1-yl)ethane-1,1-bis(phosphonate). Physico-chemical characteristics:

(i) Mass Spectrum (m/z): FAB Mass 464 (M+ +1)
(ii) Nuclear Magnetic Resonance Spectrum in CDCl$_3$, TMS internal standard):

| δ: | 1.20~1.40 | (24H, s, C(CH$_3$)(CH$_3$) ), |
|---|---|---|
| | 2.58 | (1H, t, t, J=24Hz, 8Hz, CH$_2$CH(P)(P) ), |
| | 3.54 | 2H, d, t, J=8Hz, 16Hz, CH$_2$CH), |
| | 4.60~4.90 | (4H, m, CH(CH$_3$)(CH$_3$) ), |
| | 6.80 | (1H, s, imidazole-H), |
| | 7.0~7.20 | (3H, imidazole-H) |

EXAMPLE 3

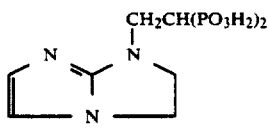

0.9 g of tetraisopropyl-2-(2,3-dihydro-1H-imidazo[1,2-a]imidazol-1-yl)ethane-1,1-bisphosphonate was dissolved in 15 ml of concentrated hydrochloric acid and heated under reflux for 2 hours. After cooling, the reaction solution was concentrated under reduced pressure to eliminate hydrochloric acid. Then, 20 ml of purified water was added to the residue and the mixture was re-concentrated under reduced pressure. The obtained yellow solid was recrystallized from water-methanol to give 0.5 g of 2-(2,3-dihydro-1H-imidazo[1,2-a]imidazol-1-yl)ethane-1,1-bis(phosphonic acid) as yellow needle-shaped crystals.

The physico-chemical characteristics of this product are as follows:

(i) m.p.: 252 to 254° C. (decomposition); (recrystallized from H$_2$O-MeOH)
(ii) Elemental Analysis (as C$_7$H$_{13}$N$_3$O$_6$P$_2$)

| | C (%) | H (%) | N (%) | P (%) |
|---|---|---|---|---|
| Calculated | 28.30 | 4.41 | 14.14 | 20.85 |
| Found | 28.10 | 4.28 | 14.06 | 20.81 |

(iii) Mass Spectrum (m/z): FAB Mass 298 (M+ +1)

In the same manner as Example 3, the following compounds were prepared.

EXAMPLE 4

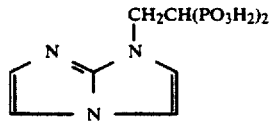

Physico-chemical characteristics:

(i) Mass Spectrum (m/z): FAB Mass 296 (M⁺ + 1)
(ii) Nuclear Magnetic Resonance Spectrum (D₂O, TMS internal standard):

| δ: | 2.30 | (1H, t, t, J=24Hz, 8Hz, C$\underline{H}$(P)(P)) |
|---|---|---|
| | 3.14 | (2H, d, t, J=8Hz, 16Hz, C$\underline{H_2}$CH), |
| | 6.90 | (2H, s, imidazole-H), |
| | 7.04 | (2H, s, imidazole-H) |

EXAMPLE 5

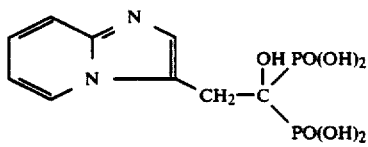

2.4 g of 2-(imidazo[1,2-a]pyridin-3-yl)acetate.hydrochloride and 2.0 g of phosphorous acid dissolved in 25 ml of chlorobenzene were heated at 110° C. under stirring for 10 minutes. Then, 5.1 g of phosphorous trichloride was added dropwise to the mixture. The mixture was further heated under stirring for 8 hours and then chlorobenzene was decanted. 45 ml of 6N-hydrochloric acid was added to the residue and the mixture was heated under reflux for 4 hours. After cooling, the mixture was treated with activated carbons and the obtained reaction solution was concentrated under pressure. The colorless solid thus obtained was recrystallized from water-methanol to give 1.3 g of 1-hydroxy-2-(imidazo[1,2-a]pyridin-3-yl)ethane-1,1-bis(phosphonic acid) in a form of colorless needle-shaped crystals.

The physico-chemical characteristics of this product are as follows:

(i) m.p.: 222 to 224° C. (decomposition); (recrystallized from MeOH-H₂O)
(ii) Elemental Analysis (as C₉H₁₂N₂O₇P₂·0.5 H₂O):

| | C (%) | H (%) | N (%) | P (%) |
|---|---|---|---|---|
| Calculated | 32.64 | 3.96 | 8.46 | 18.71 |
| Found | 32.45 | 3.91 | 8.65 | 19.05 |

(iii) Mass Spectrum (m/z): FAB Mass 323 (M⁺ + 1)

In the same manner as Example 5, the following compounds are prepared.

EXAMPLE 6

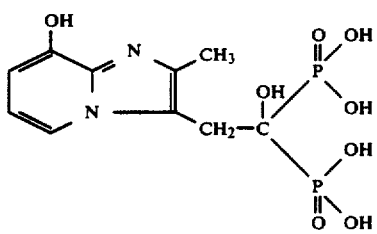

The physico-chemical characteristics:
(i) m.p.: 260 to 264° C. (decomposition); (recrystallized from MeOH-H₂O)

(ii) Elemental Analysis (as C₁₀H₁₄N₂O₈P₂·1 H₂O):

| | C (%) | H (%) | N (%) | P (%) |
|---|---|---|---|---|
| Calculated | 32.45 | 4.36 | 7.57 | 16.73 |
| Found | 32.60 | 4.11 | 7.60 | 16.44 |

(iii) Mass Spectrum (m/z): FAB Mass 353 (M⁺ + 1)

EXAMPLE 7

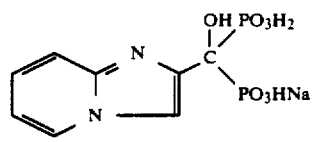

A mixture solution of 2.4 g of (imidazo[1,2-a]pyridin-2-yl) carbonic acid . hydrochloride and 2.1 g of phosphorous acid in 25 ml of chlorobenzene was heated at 110° C. under stirring for 15 minutes and then 3.6 ml of phosphorous trichloride was added dropwise. The mixture was further heated at 110° C. under stirring for 9 hours and then chlorobenzene phase was decanted. After 30 ml of 6N-hydrochloric acid was added to the residue, the mixture was heated under reflux for 6 hours. After cooling, the resulting reaction solution was treated with activated carbon and was concentrated under reduced pressure. The residue was dissolved in 20 ml of purified water. The pH of the solution was adjusted to pH 5 with 2N solution of sodium hydroxide. Then, 30 ml of methanol was added. The mixture was left at a room temperature under stirring overnight to give 0.44 g of sodium trihydrogen-1-hydroxy-1-(imidazo[1,2-a]pyridin-2-yl)methane-1,1-bis(phosphonate).

The physico-chemical characteristics of this product are as follows:
(i) m.p.: higher than 270° C. (decomposition); (recrystallized from MeOH-H₂O)
(ii) Elemental Analysis (as C₈H₉N₂O₇P₂Na):

| | C (%) | H (%) | N (%) |
|---|---|---|---|
| Calculated | 29.11 | 2.75 | 8.49 |
| Found | 29.38 | 3.06 | 8.60 |

(iii) Mass Spectrum (m/z): FAB Mass 331 (M⁺ + 1)

EXAMPLE 8

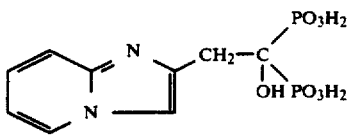

In the same manner as Example 5, 0.2 g of 1-hydroxy-2-(imidazo[2,2-a] pyridin-2-yl)ethane-1,1-bis(phosphonic acid) was prepared from 0.2 g of 2-(imidazo[1,2-a]pyridin-2-yl)acetate . hydrochloride.

The physico-chemical characteristics:
(i) Mass Spectrum (m/z): FAB Mass 323 (M⁺ + 1)
(ii) Nuclear Magnetic Resonance Spectrum

| δ | (D₂O, TMS internal standard) |
|---|---|
| 3.40 | (2H, t, J = 12Hz), |

| δ | (D$_2$O, TMS internal standard) |
|---|---|
| 6.94 | (1H, t, J = 6Hz, pyridine ring-H), |
| 7.20–7.60 | (2H, pyridine ring-H) |
| 7.84 | (1H, s, imidazole ring-H), |
| 8.10–8.20 | (1H, pyridine ring-H) |

PRESCRIPTION EXAMPLE

Examples for prescription of the compounds of the present invention as a drug will be mentioned below.

(a) Tablet:

| Compound of Example 3 | 5 mg |
|---|---|
| Lactose | 119 mg |
| Corn starch | 67 mg |
| Hydroxypropyl cellulose | 4 mg |
| Carboxymethyl cellulose Calcium | 4 mg |
| Magnesium stearate | 1 mg |
| Total | 200 mg |

After 5 g of the compound of Example 3, 119 g of lactose and 67 g of corn starch were uniformly blended, 40 ml of 10% (w/w) aqueous solution of hydroxypropyl cellulose was added thereto and the resulting mixture was granulated while wet. The granules thus obtained were blended with 4 g of carboxymethyl cellulose calcium and 1 g of magnesium stearate, and the resulting mixture is shaped into tablets each having a weight of 200 mg/tablet.

Another tablet was prepared in the same manner as above.

| Compound of Example 5 | 5 mg |
|---|---|
| Lactose | 119 mg |
| Corn starch | 67 mg |
| Hydroxypropyl cellulose | 4 mg |
| Carboxymethyl cellulose Calcium | 4 mg |
| Magnesium stearate | 1 mg |
| Total | 200 mg |

In this tablet, the same operation as above was repeated except that 5 g of the compound of Example 5 was used instead of 5 g of the compound of Example 3 in the prescription to obtain tablets each having a weight of 200 mg/tablet.

(b) Capsule:

| Compound Example 3 | 5 mg |
|---|---|
| Crystalline Cellulose | 50 mg |
| Crystalline lactose | 144 mg |
| Magnesium Stearate | 1 mg |
| Total | 200 mg |

The above-mentioned ingredients were blended each in an amount of 1,000 times of the above-mentioned amount and encapsulated in gelatin capsules so that one capsule contains 200 mg of the mixture.

Another capsule was prepared in the same manner as above.

| Compound of Example 5 | 5 mg |
|---|---|
| Crystalline Cellulose | 50 mg |
| Crystalline lactose | 144 mg |
| Magnesium Stearate | 1 mg |
| Total | 200 mg |

In this capsule, the same operation as above was repeated except that 5 g of the compound of Example 5 was used instead of 5 g of the compound of Example 3 in the prescription to prepare capsules each has a weight of 200 mg/capsule.

We claim:

1. Heterocyclic bisphosphonic acid derivatives represented by the formula:

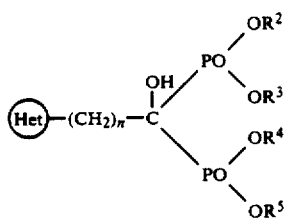

in which (Het) represents

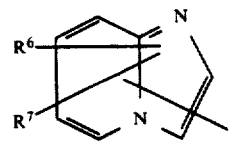

wherein $R^6$ and $R^7$ may be the same or different, each represents a hydrogen atom, a lower alkyl group, a halogen atom or a hydroxyl group, $R^2$, $R^3$, and $R^5$ may be the same or different, and each represents a hydrogen atom or a lower alkyl group, "n" is 0 or 1, or pharmaceutically acceptable salts thereof.

2. The compound set forth in claim 1 wherein said compound is 1-hydroxy-2-(imidazo [1,2-a]pyridin-3-yl)ethane-1,1-bis(phosphonic acid).

3. A bone resorption inhibitor containing as at least one active ingredient, heterocyclic bisphosphonic acid derivatives represented by the formula:

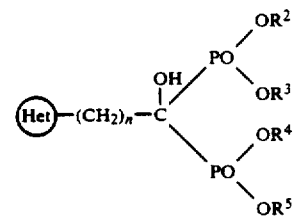

in which, (Het) represents

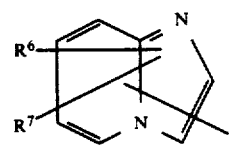

wherein $R^6$ and $R^7$ may be the same or different, each represents a hydrogen atom, a lower alkyl group, a halogen atom or a hydroxyl group, $R^2$, $R^3$, $R^4$ and $R^5$ may be the same or different, and each represents a hydrogen atom or a lower alkyl group, "n" is 0 or 1, or pharmaceutically acceptable salts thereof, and a pharmaceutically acceptable carrier.

4. The bone resorption inhibitor set forth in claim 3 wherein said heterocyclic bisphosphonic acid derivative is 1-hydroxy-2-(imidazo [1,2-a] pyridin-3-yl)ethane-1,1-bis(phosphonic acid).

5. The compound set forth in claim 1 wherein said compound is 1-hydroxy-2-(8-hydroxy-2-methylimidazo[1,2-a]pyridin-3-yl)ethane-1,1-bis(phosphonic acid).

6. The compound set forth in claim 1 wherein said compound is sodium trihydrogen-1-hydroxy-1-(imidazo[1,2-a]pyridin-2-yl)methane-1,1-bis(phosphonate).

7. The compound set forth in claim 1 wherein said compound is 1-hydroxy-2-(imidazo[1,2-a]pyridin-2-yl)ethane-1,1-bis(phosphonic acid).

* * * * *

UNITED STATES PATENT AND TRADEMARK OFFICE
CERTIFICATE OF CORRECTION

PATENT NO. : 4,990,503
DATED : February 5, 1991
INVENTOR(S) : Yasuo Isomura, et al.

It is certified that error appears in the above-indentified patent and that said Letters Patent is hereby corrected as shown below:

At Column 1, line 45;
   Column 2, line 23;
   Column 3, line 60; and
   Column 4, lines 8 and 30; that portion of the formulas reading "  " should read --  --.

Column 12, line 36; "$R^2$, $R^3$, and $R^5$" should read --$R^2$, $R^3$, $R^4$ and $R^5$--.

Signed and Sealed this

Twentieth Day of August, 1996

Attest:

BRUCE LEHMAN

Attesting Officer     Commissioner of Patents and Trademarks